US008920539B2

(12) United States Patent
Hilbig et al.

(10) Patent No.: US 8,920,539 B2
(45) Date of Patent: Dec. 30, 2014

(54) METHOD AND ARRANGEMENT FOR GENERATING OXYGEN AND NITRIC OXIDE

(75) Inventors: Rainer Hilbig, Eindhoven (NL); Achim Gerhard Rolf Koerber, Eindhoven (NL); Claudia Hannelore Igney, Erlangen (DE)

(73) Assignee: Koninklijke Philips N.V., Eindhoven (NL)

( * ) Notice: Subject to any disclaimer, the term of this patent is extended or adjusted under 35 U.S.C. 154(b) by 72 days.

(21) Appl. No.: 13/822,672

(22) PCT Filed: Sep. 14, 2011

(86) PCT No.: PCT/IB2011/054018
§ 371 (c)(1),
(2), (4) Date: Mar. 13, 2013

(87) PCT Pub. No.: WO2012/038860
PCT Pub. Date: Mar. 29, 2012

(65) Prior Publication Data
US 2013/0177657 A1 Jul. 11, 2013

(30) Foreign Application Priority Data

Sep. 22, 2010 (EP) .................................... 10178293
Mar. 3, 2011 (EP) .................................... 11156845

(51) Int. Cl.
*B01D 53/22* (2006.01)
*B01D 63/00* (2006.01)
*C01B 13/02* (2006.01)
*A61K 33/00* (2006.01)
*C01B 21/24* (2006.01)

(52) U.S. Cl.
CPC ................ *A61K 33/00* (2013.01); *B01D 63/00* (2013.01); *C01B 13/0251* (2013.01); *C01B 21/24* (2013.01)
USPC .............. 95/54; 95/43; 95/45; 96/4

(58) Field of Classification Search
USPC ......................... 95/43, 45, 54; 96/4
See application file for complete search history.

(56) References Cited

U.S. PATENT DOCUMENTS 5,472,680 A    12/1995  Reimer et al.
5,954,859 A *  9/1999   Keskar et al. ................ 95/54
(Continued)

OTHER PUBLICATIONS

X. Hou et al., "(no title)", J. Fuel Chem Technol 2007, 35(04), pp. 501-504.

(Continued)

*Primary Examiner* — Jason M Greene
*Assistant Examiner* — Anthony Shumate

(57) ABSTRACT

The invention relates to a Method of generating oxygen and nitric oxide. The method comprises the steps of: guiding an oxygen comprising gas to a primary side of a dense membrane (42), heating the membrane (42) to a temperature at which it is permeable for oxygen, creating a pressure difference between the primary side of the membrane (42) and a secondary side of the membrane (42), wherein a stream of oxygen is generated at the secondary side of the membrane (42) and a stream of oxygen depleted gas is generated at the primary side of the membrane (42). The method according to the invention further comprises the steps of: providing a flow of nitrous oxide comprising gas and heating the nitrous oxide comprising gas to a temperature at which nitric oxide is generated. Thereby, according to the invention, heat generated in the process of operating the membrane is used. According to the invention it is possible to generate both oxygen and nitric oxide in one device making use of several synergistic effects, thus being energy saving.

15 Claims, 2 Drawing Sheets

(56) References Cited

U.S. PATENT DOCUMENTS

| | | | |
|---|---|---|---|
| 6,139,604 A * | 10/2000 | Gottzmann et al. | 95/54 |
| 6,328,941 B1 | 12/2001 | Watzenberger et al. | |
| 6,500,398 B1 | 12/2002 | Tagawa et al. | |
| 6,623,714 B2 | 9/2003 | Shreiber et al. | |
| 7,165,546 B2 | 1/2007 | Frankie et al. | |
| 8,012,446 B1 * | 9/2011 | Wright et al. | 423/437.1 |
| 8,410,182 B2 * | 4/2013 | Wood et al. | 516/10 |
| 2005/0139067 A1 | 6/2005 | Shreiber et al. | |
| 2007/0061393 A1 * | 3/2007 | Moore | 709/201 |
| 2007/0106537 A1 * | 5/2007 | Moore | 705/3 |
| 2007/0106752 A1 * | 5/2007 | Moore | 709/217 |
| 2007/0116037 A1 * | 5/2007 | Moore | 370/462 |
| 2008/0115773 A1 * | 5/2008 | Gaur et al. | 123/585 |
| 2012/0067304 A1 * | 3/2012 | Littmann | 123/3 |
| 2012/0258034 A1 * | 10/2012 | Hilbig et al. | 423/405 |
| 2014/0000473 A1 * | 1/2014 | Miller | 104/138.1 |

OTHER PUBLICATIONS

Unknown Author, "Production of Oxygen by Integrated Ion Transport Membrane Systems", Originally published in Research Disclosure, Jun. 1995, Publ. No. 37438, pp. 427-440.

B.G. Reuben et al., "Thermal Decomposition of Nitrous Oxide", Transactions of the Faraday Society, Butterworths Scientific Publications Ltd. London, GB, vol. 55, Jan. 1, 1959, pp. 1543-1553.

J.A. Yagiela, "Health Hazards and Nitrous Oxide: A Time for Reappraisal", Anesthesia Progress, New York, NY, US, vol. 38, 1991, pp. 1-11.

M. Yoshida et al., "Combined Inhalation of Nitric Oxide and Oxygen in Chronic Obstructive Pulmonary Disease", American Journal of Respiratory and Critical Care Medicine, American Lung Association, New York, NY, US, vol. 155, No. 2, Feb. 1, 1997, pp. 526-529.

* cited by examiner

METHOD AND ARRANGEMENT FOR GENERATING OXYGEN AND NITRIC OXIDE

FIELD OF THE INVENTION

The invention relates to the field of oxygen separation. The invention further relates to the field of nitric oxide generation. Particularly, the invention relates to oxygen separation and nitric oxide generation for therapeutic applications, particularly in the field of home care.

BACKGROUND OF THE INVENTION

Oxygen therapy is the administration of oxygen as a therapeutic modality. It is widely used for a variety of purposes in both chronic and acute patient care as it is essential for cell metabolism, and in turn, tissue oxygenation is essential for all physiological functions. Oxygen therapy should be used to benefit the patient by increasing the supply of oxygen to the lungs and thereby increasing the availability of oxygen to the body tissues, especially when the patient is suffering from hypoxia and/or hypoxemia. Oxygen therapy may be used both in applications in hospital or in home care. The main home care application of oxygen therapy is for patients with severe chronic obstructive pulmonary disease (COPD).

Oxygen may be administered in a number of ways. A preferable way of oxygen administration is by using a so called on demand generation of oxygen. Referring to this, commercial solutions, so-called oxygen concentrators or separators, respectively, are widely known. These oxygen concentrators mostly separate oxygen from an oxygen comprising gas, so that the oxygen is provided on demand, i.e. directly before use. Most known oxygen concentrators require a compressor to compress the oxygen comprising gas. Furthermore, oxygen, preferably pure oxygen, has to be generated. Most known oxygen concentrators thus comprise an organic membrane to separate oxygen from the oxygen comprising gas.

The major drawbacks of the known oxygen concentrators are high costs and a limited convenience with respect to noise. Furthermore, undesired constituents of the oxygen comprising gas, mostly nitrogen, are adsorbed on the membrane thereby causing the requirement of a so-called swing process by which the adsorbed gas is desorbed from the membrane. During that desorption step, a separation of oxygen is not possible, because of which two membranes are desired which further increases the costs. Apart from that, the compressors are mostly noisy leading to a decreased convenience especially when the oxygen concentrator is used overnight. Furthermore, the generated oxygen is non-sterile, because of which a further measure of disinfection is often desired or necessary.

Known from U.S. Pat. No. 6,623,714 B2 is a method of separating oxygen from an oxygen comprising gas with the use of a ceramic membrane unit. According to this method, a feed stream is compressed and heated afterwards, and the heated and compressed stream of oxygen comprising gas is then guided through a heated ceramic membrane. Due to the properties of the ceramic membrane being located in the membrane unit, an oxygen permeate is formed composed of at least a portion of the oxygen contained within the compressed feed stream and consequently a retentate is formed containing at least a portion of the residual components of said compressed feed stream.

However, especially for therapeutic applications being directed to the treatment of COPD, it is discussed that a certain amount of nitric oxide enhances the therapeutic effect. Consequently, additionally to an arrangement for generating oxygen, an arrangement for generating nitric oxide may be provided. The nitric oxide or a gas comprising the latter may then be guided into the stream of oxygen, or oxygen comprising gas, respectively.

SUMMARY OF THE INVENTION

It is an object of the present invention to provide a method and an arrangement for generating oxygen and nitric oxide which is easy to perform, cost-saving, and/or which is advantageous with respect to maintenance and noise.

These objects are achieved by a method of generating oxygen and nitric oxide, said method comprising the steps of: guiding an oxygen comprising gas to a primary side of a dense membrane, heating the membrane to a temperature at which it is permeable for oxygen, creating a pressure difference between the primary side of the membrane and a secondary side of the membrane, wherein a stream of oxygen is generated at the secondary side of the membrane and a stream of oxygen depleted gas is generated at the primary side of the membrane, wherein said method further comprises the steps of providing a flow of nitrous oxide comprising gas, heating the nitrous oxide comprising gas to a temperature at which nitric oxide is generated, thereby using heat generated in the process of operating the membrane.

The term dense membrane, as used herein, shall refer to a membrane which is permeable for oxygen but non-permeable for other gases, especially for nitrogen. Consequently, a dense membrane is suitable for separating oxygen from an oxygen comprising gas, thereby generating pure or essentially pure oxygen. Additionally, the term oxygen comprising gas, as used herein, shall refer to any gas which at least partly comprises oxygen, whereas the term nitrous oxide comprising gas, as used herein, shall refer to any gas which at least partly comprises nitrous oxide. Furthermore, the term primary side of the membrane, as used herein, shall refer to the side of the membrane being directed towards the direction the oxygen comprising gas is guided to the membrane, whereas the term secondary side of the membrane, as used herein, shall refer to the side of the membrane being directed towards the opposite side, i.e. to the side at which the generated pure oxygen is present.

Additionally, the step of heating the nitrous oxide comprising gas to a temperature at which nitric oxide is generated, thereby using heat generated in the process of operating the membrane shall mean that the heat being generated in order to heat the membrane to its operational temperature is used for heating the nitrous oxide comprising gas. In detail, in case the membrane is heated by a heating device, the heating device may be used for heating the nitrous oxide comprising gas or the heated membrane as such may be used. In case the membrane is heated indirectly by heating the oxygen comprising gas and bringing in contact the oxygen comprising gas with the membrane, the hot gas may be used for heating the nitrous oxide comprising gas. The heating effect may thereby be performed directly, for example by bringing in contact the nitric oxide comprising gas with the hot gas or with the vicinity of the membrane, or indirectly, by using a heat exchanger.

According to the invention, the generation of pure oxygen is thus combined with the generation of nitric oxide in one device and essentially in one step. This leads to the provision of very beneficial synergistic effects. In detail, a reaction to generate nitric oxide is based on nitrous oxide as starting material. In this case, the reaction requires energy, especially in the form of elevated temperatures, the nitrous oxide, or the nitrous oxide comprising gas, respectively, is heated to. This energy, or these elevated temperatures, respectively, are present due to the fact the dense membrane requires elevated temperatures in order to separate oxygen from the oxygen comprising gas, or the remaining components thereof, respectively, especially in the case an inorganic membrane is used. Consequently, by using heat generated in the process of operating the membrane, the nitrous oxide comprising gas is heated as well. Thus, a heating device for heating the nitrous oxide comprising gas may be omitted, allowing the method according to the invention being performed with a considerable decrease of energy.

Furthermore, particularly by utilizing a dense inorganic membrane, oxygen may be provided with a high purity, which may be more than 99% and up to 100% depending on the used membrane and the adjusted reaction conditions. In order to heat the membrane and thus to allow the membrane being permeable for oxygen in a suitable amount, a heating device may be provided. However, it is preferred to heat the membrane just by heating the oxygen comprising gas to a suitable amount. Consequently, the membrane may be heated directly, for example via a heating device, or indirectly, for example via a heated gas stream.

Additionally and with respect to the nitric oxide generation, according to the invention, the method starts from nitrous oxide as precursor. The usage of such a precursor is very beneficial. First of all, it is cheap leading to the method according to the invention being carried out in a cost-saving manner. Furthermore, nitrous oxide is an inert gas. This leads to the possibility of storing it safely for a substantially unlimited time e.g. in a gas cylinder or the like. During the storing time, there is no risk of undesired side products to be formed, especially there is no risk of the formation of toxic nitrogen oxides. Additionally, nitrous oxide as such is non-toxic in a wide range of concentrations. This offers the benefit that the method according to the invention may be carried out in situ even with respect to therapeutic applications. If some or even a major amount of nitrous oxide stays unreacted in the nitrous oxide comprising gas, no health risk will appear by administering the formed nitric oxide comprising gas directly to a patient, because the nitrous oxide concentration used will be in a limited concentration as the nitrous oxide is mixed with the gas stream being generated in the respective membrane chamber.

Furthermore, no other radicals except nitric oxide and nitrogen dioxide may be formed during the method according to the invention. This leads to the reaction being carried out in a well defined manner and with well defined products. Nearly no undesired side reaction will appear deteriorating the generated gas.

Additionally, it has to be noted that according to the invention, the concentration of nitrogen dioxide in the nitric oxide comprising gas is always below the security limit during every stage of the process. Therefore, there is no health risk even by applying the method according to the invention in situ with respect to therapeutic applications. This effect is mainly due to the fact that the generated gas comprising nitric oxide will be heated to a temperature in a range the dense membrane is working. At these temperatures, however, the formation of nitrogen dioxide is thermodynamically inhibited. In detail, particularly at temperatures above 600K, the formation of nitrogen dioxide is inhibited.

Furthermore, due to the fact that the output concentration of nitric oxide is a certain fraction of the nitrous oxide start concentration, the obtained nitric oxide comprising gas offers a well defined concentration of nitric oxide. This concentration may further be very well adjusted by varying the process parameters. Said nitric oxide concentration may thus be adapted very well to a number of desired applications even by using a low starting concentration of nitrous oxide. In particular, the obtained concentration covers the range for therapeutic applications, or medical applications, respectively.

The step of heating the nitrous oxide comprising gas to a temperature which is sufficiently high to enable a reaction of nitrous oxide to form nitric oxide thereby allows a conversion of nitrous oxide to nitric oxide without the use of a catalyst. This is especially advantageous as a catalyst most likely catalyzes undesired side reactions. In particular, the formation of nitrogen and oxygen will be activated by a catalyst.

In a preferred embodiment of the present invention the flow of nitrous oxide comprising gas is guided into one of the stream of oxygen and the stream of oxygen depleted gas. This embodiment allows directly mixing the stream of nitrous oxide comprising gas with the stream of oxygen or oxygen depleted gas allowing a broad variety of applications. Additionally, especially in case these gas streams are heated in order to heat the membrane, the heating step of the nitrous oxide comprising gas is especially effective. The nitrous oxide comprising gas may thus be guided and mixed with the respective gas stream directly after the generation process, i.e. when the gas stream is depleted with respect to oxygen at the primary side of the membrane or when the stream of oxygen is generated at the secondary side of the membrane. For example, the flow of nitrous oxide comprising gas may be guided into a primary membrane chamber being located at the primary side of the membrane or into a secondary membrane chamber being located at the secondary side of the membrane.

With respect to the primary side of the membrane, or the primary membrane chamber, respectively, the nitrous oxide comprising gas is guided to the side of the membrane being directed to the source of oxygen comprising gas. This embodiment allows forming a nitric oxide comprising gas in an atmosphere in which the main component is nitrogen due to the fact that this atmosphere is depleted with respect to oxygen. This considerably reduces the danger of nitrogen dioxide to be formed both in a hot as well as in a cold atmosphere. In fact, the formation of nitrogen dioxide is substantially inhibited. Accordingly, the generated nitric oxide comprising gas may be stored, for example in a gas reservoir, in order to use it at a different point of time. Alternatively, the nitric oxide comprising gas may be used directly. Therefore, it is possible to guide it into the stream of generated oxygen. This allows generating an oxygen and nitric oxide comprising gas in various concentrations. Consequently, there is a high flexibility with respect to using the generated nitric oxide comprising gas.

Additionally, the nitrous oxide comprising gas may be guided into a stream of gas being depleted with respect to oxygen downstream the membrane unit. This embodiment allows guiding the nitrous oxide comprising gas into a small amount of the gas stream being generated at the primary side of the membrane. It may thus strictly be excluded that oxygen is present in the gas stream. Additionally, due to the hot temperatures in the membrane unit, the temperature of the gas stream is still high enough to allow nitric oxide to be formed. Apart from that, as only a limited amount of gas stream is used, less nitrous oxide is required for achieving the desired amount of nitric oxide in that gas stream. Due to the fact that a considerably bigger volume of gas being depleted with respect to oxygen is generated with respect to pure oxygen, a limited amount of depleted gas stream will in most cases be sufficient to get a desired nitric oxide concentration in a combined application of nitric oxide comprising gas and oxygen.

With respect to guiding the flow of nitrous oxide comprising gas to the secondary side of the membrane, for example into the secondary membrane chamber the nitrous oxide comprising gas is guided to the side of the membrane being directed opposite to the source of oxygen comprising gas. This embodiment allows directly forming a mixture of pure oxygen and nitric oxide comprising gas. Consequently, the generated gas may comprise a mixture which may be administered to a patient directly without further mixing steps, an administration to a patient is thus possible by directly guiding it to an administration device such as a mask. However, due to the fact that the formation of nitrogen dioxide is only inhibited at elevated temperatures, especially at temperatures ≥600K, the formed gas mixture should be cooled to room temperature, for example, shortly before administering it to a patient, or before guiding it into an administration device, respectively, in order to avoid or at least considerably reduce the formation of nitrogen dioxide.

Apart from that it may be preferred to branch off a defined part of the oxygen comprising gas before it reaches the membrane unit and to guide the nitrous oxide comprising gas into this gas stream. In this case, the oxygen comprising gas may be either heated before mixing it with the nitrous oxide comprising gas, or the mixture of the respective gas streams may be heated by means of a heat exchanger, for example, the latter being driven by the heat being generated in the process of operating the membrane. In this case, a nitric oxide comprising gas may be generated independently from the further gas streams, particularly from the oxygen stream and the stream of oxygen depleted gas.

In a further preferred embodiment of the present invention the oxygen comprising gas is compressed in order to create a pressure difference between the primary side and the secondary side of the membrane. This is an especially preferred embodiment due to the fact that by compressing the oxygen comprising gas on the one hand the latter is already heated due to physical reasons. Additionally, this is an especially easy way to create a well-defined and stable pressure difference between the primary and the secondary side of the membrane.

In a further preferred embodiment of the present invention the oxygen comprising gas is compressed by a plasma pump. This embodiment according to the invention allows realizing a device for compressing the oxygen comprising gas and a device for heating the membrane unit in one single device. By using a plasma pump, the present invention utilizes the finding that a combination of heating and compressing an oxygen comprising gas in a plasma pump especially together with separating the oxygen by an inorganic membrane leads to surprising and very beneficial synergistic effects. In detail, the oxygen comprising gas is compressed and heated in one step. This leads to the advantage that an additional device for heating the compressed gas or the membrane as such is not required. Contrary thereto, the gas which leaves the plasma pump has a sufficiently high temperature to heat the membrane thereby enabling a sufficiently high oxygen flow through said membrane. Thus, the generally undesired effect, that, by compressing a gas with a plasma pump, the compressed oxygen comprising gas has an elevated temperature, is very well applicable in combination with an inorganic membrane.

Furthermore, a plasma pump works with a reduction of noise leading to a considerable increase in convenience, especially in home care applications. The convenience is even more improved by the fact that by providing a plasma pump for heating and compressing the oxygen comprising gas, the used device has reduced size and weight which is particular advantageous for home care applications.

Additionally, by using an arrangement with both a plasma pump and an inorganic membrane, oxygen is separated with lower costs due to the fact that the arrangement as such may be designed much cheaper, and furthermore, the energy efficiency is improved compared to the methods known from the state of the art.

A further advantage of the method according to this embodiment of the present invention is the generation of sterile oxygen. Additional disinfection or sterilization steps are not necessary. According to the invention, an on demand generation of sterile oxygen is provided.

By using a plasma pump instead of a compressor known from the state of the art an increase with respect to cost price, servicing and noise may thus be achieved.

Alternatively, it may be preferred that the membrane is heated by a heating device. This embodiment allows heating the membrane directly which enables adapting the method according to the invention to membrane systems known from the art.

In a further preferred embodiment of the present invention the oxygen comprising gas is compressed to a range of ≥2.5 bars. By compressing the oxygen comprising gas to such an amount, the generated oxygen will come up with an oxygen pressure above atmospheric pressure on the secondary side. This pressure may be enough to get a sufficiently high oxygen flow through the membrane providing an adequate flow of generated pure oxygen. Referring to this, it is particularly advantageous, if the oxygen comprising gas is compressed to a range of 5 bars. This embodiment consequently particularly allows working without a further pump on the secondary side. In contrast thereto, the generated oxygen may be guided to the desired application directly after use solely by the force of the compression step of the oxygen comprising gas.

In a further preferred embodiment of the present invention the nitrous oxide comprising gas is formed by mixing nitrous oxide with at least a part of the oxygen depleted gas. This embodiment thus forms the nitrous oxide comprising gas based on a carrier gas which mainly comprises nitrogen. Consequently, a gas mixture is formed which mainly comprises nitrogen and nitrous oxide. This is a very stable mixture being well suitable for the generation of nitric oxide. Furthermore, the desired concentration of nitrous oxide may be adjusted in an easy manner. Additionally, no further source for generating the nitrous oxide comprising gas is required, but the gas being depleted with respect to oxygen and which is generated in any case is recycled. Consequently, the method according to this embodiment is especially cost-saving and furthermore resource-saving. Apart from that, the nitrous oxide comprising gas is generated by using a gas which already exhibits elevated temperatures. Consequently, it is not necessary to heat the nitrous oxide comprising gas to a big extend. The method according to this embodiment is thus especially energy-saving. Furthermore, the reaction may start for example essentially directly after the nitrous oxide comprising gas reaches the respective gas stream, resulting in considerably reduced reaction times.

In a further preferred embodiment of the present invention nitric oxide is generated based on a gas in which nitrous oxide is present in a concentration in the range of ≤2 vol-%. In case mixing the nitrous oxide comprising gas with one of the oxygen comprising gas, the oxygen depleted gas or the oxygen this shall particularly mean the nitrous oxide concentration in the gas stream after mixing the nitrous oxide comprising gas with the respective further gas stream. According to this embodiment, several advantages may be achieved. On the one hand, the concentration of the generated gas will lead to a concentration of nitric oxide which is adjusted to be in a suitable range for numerous applications. For example, the concentration will be in the range being required for therapeutic applications, for example with respect to dealing with COPD. On the other hand, by using a concentration of nitrous oxide like described above, even if some or even a major amount of nitrous oxide stays unreacted, no health risk will appear by administering the generated gas directly to a patient, because the nitrous oxide concentration will be far too low to present a security risk. Apart from that, due to the low concentration of nitrous oxide and consequently due to the low concentration of generated nitric oxide, the danger of nitrogen oxides in higher oxidation states to be formed is further reduced. This is due to the fact that the formation of nitrogen dioxide, for example, is strongly dependent from the concentrations of the starting materials, i.e. nitric oxide, for example.

However, it is preferred to adapt the concentration dependent from the mixture of the respective gas stream and the nitrous oxide comprising gas. If the nitrous oxide comprising gas is guided into the oxygen depleted gas at the primary side of the membrane, a rather high concentration of nitrous oxide may be used. In detail, a nitrous oxide concentration of up to 2 vol-% may be used, e.g. in a range of ≥0.2 vol-% to ≤2 vol-%.

In case the nitrous oxide comprising gas is guided into the stream of oxygen at the secondary side of the membrane, a rather low concentration of nitrous oxide may be used. In detail a nitrous oxide concentration of ≤0.1 vol-% may be appropriate. Due to the fact that the formation of nitrogen dioxide is dependent from the concentration of nitric oxide, when the generated gas is cooled, the risk of generating high amounts of nitrogen dioxide will increase by using higher nitrous oxide concentrations resulting in higher nitric oxide concentrations.

In case the nitrous oxide comprising gas is guided into a stream of oxygen comprising gas, the concentration may as well be ≤2 vol-% in order to inhibit the formation of nitrogen dioxide to a big extend.

However, it is to be noted that the above concentrations are mainly set in order to inhibit or reduce the formation of toxic gases. Consequently, the defined concentrations are mainly preferred in case the generated gas stream is used in the field of therapeutic applications. In case a higher amount of nitrogen dioxide in the nitric oxide comprising gas is not detrimental, the concentration of nitrous oxide may be higher.

Generally, with respect to the flow of nitrous oxide comprising gas being guided to the primary or secondary side of the membrane, it is preferred to use only a minor amount of carrier gas, but to have a high concentration of nitrous oxide. It may be preferred to use pure nitrous oxide.

It is clear to one skilled in the art that that the average concentration in the respective gas stream, for example, is meant as the concentration may vary. For example, the concentration at an inlet, where the nitrous oxide comprising gas is inserted into the gas stream may be higher.

In a further preferred embodiment of the present invention air is used as oxygen comprising gas. This is especially preferable at home care applications because no special oxygen comprising gases have to be stored. In contrast thereto, the air surrounding an arrangement for performing the method according to the invention may be used as oxygen comprising gas. Consequently, the weight as well as the dimensions of an arrangement being used for carrying out the present invention may be reduced. This allows a strong improvement with respect to convenience.

In a further preferred embodiment of the present invention the oxygen comprising gas is heated to a temperature in the range of ≥1000 K and ≤1300 K. By providing an accordingly heated oxygen comprising gas, the membrane is heated to a sufficiently high temperature to provide adequate permeability properties for oxygen. Apart from that, the membrane exhibits a temperature which is high enough for ensuring that adequate conditions are formed with respect to a reaction of nitrous oxide to form nitric oxide. Additionally, the nitrous oxide comprising gas, or the nitric oxide comprising gas, respectively is heated to an amount, at which the generation of nitrogen dioxide is thermodynamically hindered. Consequently, a method according to this embodiment achieves a further advantage with respect to security.

In a further preferred embodiment of the present invention the generated oxygen is cooled after separation. This enables a direct administration of oxygen to the patient. The cooling procedure may thereby be adapted to the specific use. In some applications, it is desirable if the oxygen is cooled down to room temperature whereas some applications are more effective when using oxygen at temperatures being elevated with respect to room temperature. Especially in case nitric oxide is generated in the stream of oxygen, the generated oxygen, together with the nitric oxide, should be cooled shortly before the administration step.

In a further preferred embodiment of the present invention the reaction time of the nitrous oxide comprising gas lies in a range of ≥10 ms to ≤100 s, in particular in a range of ≥0.1 s to ≤30 s. These reaction times may lead to an adequate conversion at rather smooth reaction conditions. Additionally, the reaction times are short enough to generate a sufficiently high amount of nitric oxide comprising gas in a time scale which may be appropriate even for an in situ generation of nitric oxide, in particular for therapeutic applications. The reaction time of the nitrous oxide comprising gas shall thereby particularly mean the average time at which the nitrous oxide comprising gas is present in hot regions, especially with T>1000 K. For example, the reaction time may be defined as the time during which the nitrous oxide comprising gas is present in the respective membrane chamber.

In a further preferred embodiment of the present invention SATP flow rates of the nitrous oxide comprising gas of ≥0.1 $L_{SATP}$/min to ≤10 $L_{SATP}$/min are used. In particular flow rates of 0.4 $L_{SATP}$/min are used, wherein "$L_{SATP}$" means the amount of gas in 1 L volume at standard ambient temperature (25° C.; 298.15K) and pressure (1 bar). This leads to the nitrous oxide comprising gas having a sufficiently long reaction time even if, for example, the membrane unit is designed in very small dimensions. The reaction time may be defined as $t=(V_r*p_r*298.15K)/(q^\Theta*1\ bar*T_r)$, wherein $V_r$ means the volume of the respective chamber, for example, in the membrane unit at reaction temperature, $p_r$ means the reaction pressure, $T_r$ means the reaction temperature and $q^\Theta$ means the SATP flow rate. Furthermore, these flow rates are very well suited for an in situ generation of nitric oxide and to administer the formed gas directly without the need of (pre-) storing it.

The invention further relates to an Arrangement for generating oxygen and nitric oxide, the arrangement comprising a source of oxygen comprising gas, a dense membrane having a primary side and a secondary side, a device for creating a pressure difference between the primary side and the secondary side of the membrane, and a device for heating the membrane, wherein the arrangement further comprises a source of nitrous oxide comprising gas, and a device being designed for heating a flow of nitrous oxide comprising gas being egressed from the source of nitrous oxide comprising gas to a temperature, at which nitric oxide is generated, using heat generated in the process of operating the membrane. This arrangement is designed to perform the method according to the invention. Consequently, the arrangement exhibits the advantages described with respect to the method according to the invention.

According to the invention, the arrangement comprises a source of oxygen comprising gas and a source of nitrous oxide comprising gas. These gas sources may be any known gas sources being configured for providing an oxygen comprising gas and a nitrous oxide comprising gas, respectively. The gas sources may be gas storing devices, such as gas cylinders, or devices for generating the respective gas in-situ. Additionally, the source of oxygen comprising gas may be the air surrounding the arrangement according to the invention.

The device for creating a pressure difference between the primary and the secondary side of the membrane may for example be a vacuum pump being arranged at the secondary side of the membrane. Additionally, the device may be a compressor, a pump, or the like being designed for compressing the oxygen comprising gas at the primary side of the membrane.

Furthermore, the device for heating the membrane may be a heating element. Consequently, there may be provided separated devices, one being designed to heat the membrane and one being designed to create a pressure difference. However, it is furthermore possible to include a compressing device, for example, as well as a heating device in one single device, wherein the gas may be heated and compressed in one step. Due to the fact that the heated gas will be guided to the membrane, the latter is heated by means of the heated gas. Furthermore, the device for compressing the oxygen comprising gas and the device for heating the membrane may be realized in one single device.

A dense membrane according to the invention shall thereby mean a membrane being permeable with respect to oxygen, but being strictly or at least substantially non-permeable for other gases, especially for nitrogen.

The device being designed for heating a flow of nitrous oxide comprising gas being egressed from the source of nitrous oxide comprising gas to a temperature, at which nitric oxide is generated, using heat generated in the process of operating the membrane may be configured in any desired way. It should however use the heat being required for heating the membrane to its operational temperature or the heat of the membrane as such in order to heat the nitrous oxide comprising gas, so that no further heating device is required for heating the nitrous oxide comprising gas.

In a preferred embodiment of the present invention, the device being designed for heating a flow of nitrous oxide comprising gas comprises a conduit being arranged to guide the nitrous oxide comprising gas to the primary side of the membrane or to the secondary side of the membrane. This conduit may be any conduit, or connection, respectively, through which the nitrous oxide comprising gas may be selectively guided for example into the respective gas stream. For example, it may be guided into a primary and/or secondary membrane chamber. Therefore, the conduit may be formed as a pipe being connected to a source of nitrous oxide comprising gas going through a wall of the membrane unit and proceeding preferably to the vicinity of the membrane, to its primary or its secondary side, in the respective membrane chamber. Additionally, the conduit may be arranged to guide the nitrous oxide comprising gas to the gas stream being generated in the primary membrane chamber but downstream the latter, or into a stream of oxygen comprising gas being branched off the main stream of oxygen comprising gas upstream the membrane unit.

In a further preferred embodiment of the present invention, the device being designed for heating a flow of nitrous oxide comprising gas comprises a heat exchanger. This allows heating the nitrous oxide comprising gas without a direct contact of the nitrous oxide comprising gas, or the nitric oxide comprising gas, respectively, with a further gas stream.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
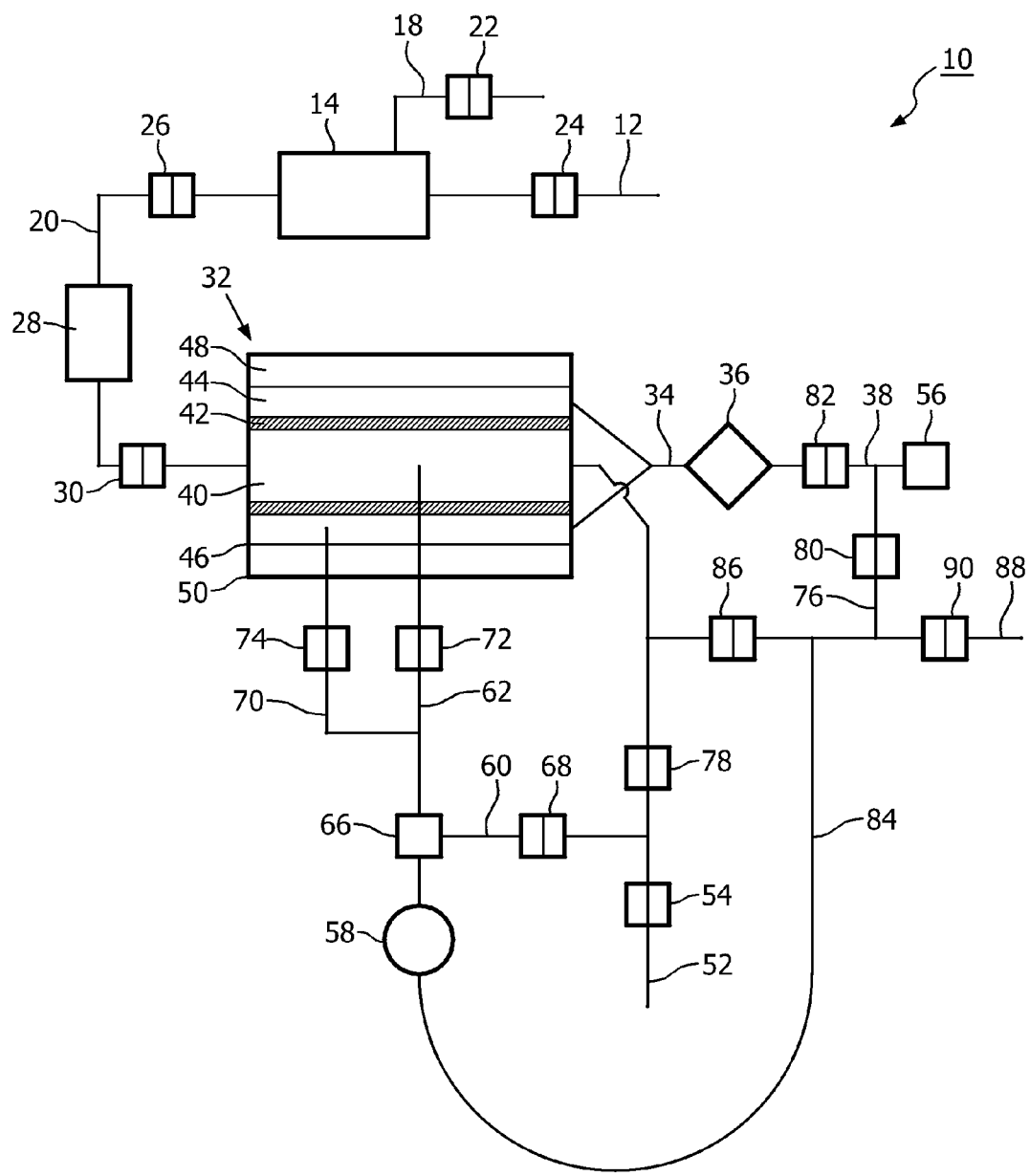
FIG. 1 shows a schematic cross sectional view of an arrangement according to the invention.

In FIG. 1, a preferred embodiment of an arrangement 10 for generating oxygen and nitric oxide is schematically shown. The arrangement 10 is very well suitable for therapeutic applications, especially in the field of COPD treatment e.g. in home care applications. However, the arrangement 10 as well as the method according to the invention is not limited to therapeutic applications.

The arrangement 10 comprises a gas inlet 12 for guiding oxygen comprising gas into the arrangement 10. In order to compress the oxygen comprising gas, a compressing device may be provided. Additionally, a device for heating the oxygen comprising gas may be provided, wherein both devices may be combined in one single device. For example, the single device may be a plasma pump 14. In the following, the invention is described in a non-limiting manner with respect to a plasma pump 14. However, it hast to be noted that the following description of the arrangement 10 is possible with any device or devices being designed to compress and preferably to heat the oxygen comprising gas.

A plasma pump 14 is known to one skilled in the art and is only briefly discussed here. The plasma pump 14 may comprise a discharge chamber in which a gas discharge is formed and thus a plasma is generated, for example by use of an alternating current. The discharge chamber may further comprise a gas inlet, which may be connected to the gas inlet 12 or which may be part of the latter. Additionally, the plasma pump 14 may comprise a first gas outlet 18 and a second gas outlet, the latter being connected to a conduit 20. The first gas outlet 18 may further comprise an exhaust device 22 which may be designed as a simple two way valve. It is on one side connected to the discharge chamber and on the other side connected to the atmosphere or a reservoir for exhaust gas. The discharge chamber is further connected to the second gas outlet. Generally, a valve according to the invention may be any device which may allow, inhibit and/or regulate the flow of a gas stream. To control gas flow through the gas inlet and the second gas outlet, an inlet valve 24 is connected to the gas inlet and an outlet valve 26 is connected to the second gas outlet. As inlet valve 24 and outlet valve 26, non-return valves or two-way valves can be used, for example. Non-return valves are preferred because they do not need controlling. By adapting the operation of the inlet valve 24 and the outlet valve 26 to a power modulated gas discharge, a gas flow can be generated with a specific direction.

Generally, a rather small energy input for the plasma pump 14 is sufficient. In detail, a power input of 100 W to 350 W may be sufficient depending on the temperature and membrane conditions. This range of power input is very well suitable for home care applications.

By generating a plasma in the discharge chamber like described above, a pressurized and heated oxygen comprising gas is generated. Consequently, the plasma pump may function as a gas pump allowing generating a direct and continuous flow of oxygen comprising gas.

To further support a continuous flow, it is preferable to provide a gas reservoir 28 downstream the outlet valve 26. By pressing oxygen comprising gas from the discharge chamber into the gas reservoir 28, an over pressure inside the reservoir 28 can be generated, preferably by increasing the flow resistance downstream the gas reservoir 28 by providing a reservoir valve 30 or, alternatively, an orifice. A constant or nearly constant over pressure can be used to generate a continuous or nearly continuous flow of the oxygen comprising gas in the conduit 20.

In the following, the compressed and heated oxygen comprising gas may enter, through the conduit 20, a membrane unit 32 for separating oxygen from the oxygen comprising gas, i.e. to generate oxygen. Downstream the membrane unit 32, a conduit 34 may guide the generated pure oxygen to a cooler 36 downstream of which an outlet 38 is provided for administration of the oxygen. The cooling of cooler 36 may be done by a forced air stream using the surrounding air, for example by using a ventilator or the like. The working mode with respect to oxygen separation of the arrangement 10 is described in more detail below.

Downstream the plasma pump 14 or the reservoir 28, respectively, the oxygen comprising gas is guided to the membrane unit 32. Upstream the membrane unit 32, a valve may be provided, which may be the reservoir valve 30 or an additional valve. This valve may close the conduit 20, when the pressure of the oxygen comprising gas is insufficient. Contrary thereto, the valve may open the conduit 20 when a sufficiently high pressure is reached. Thus, it may be provided that at a pressure of ≥2.5 bars, in particular at 5 bars, the valve opens, thus guiding the oxygen comprising gas to the membrane unit 32.

Figure 2:
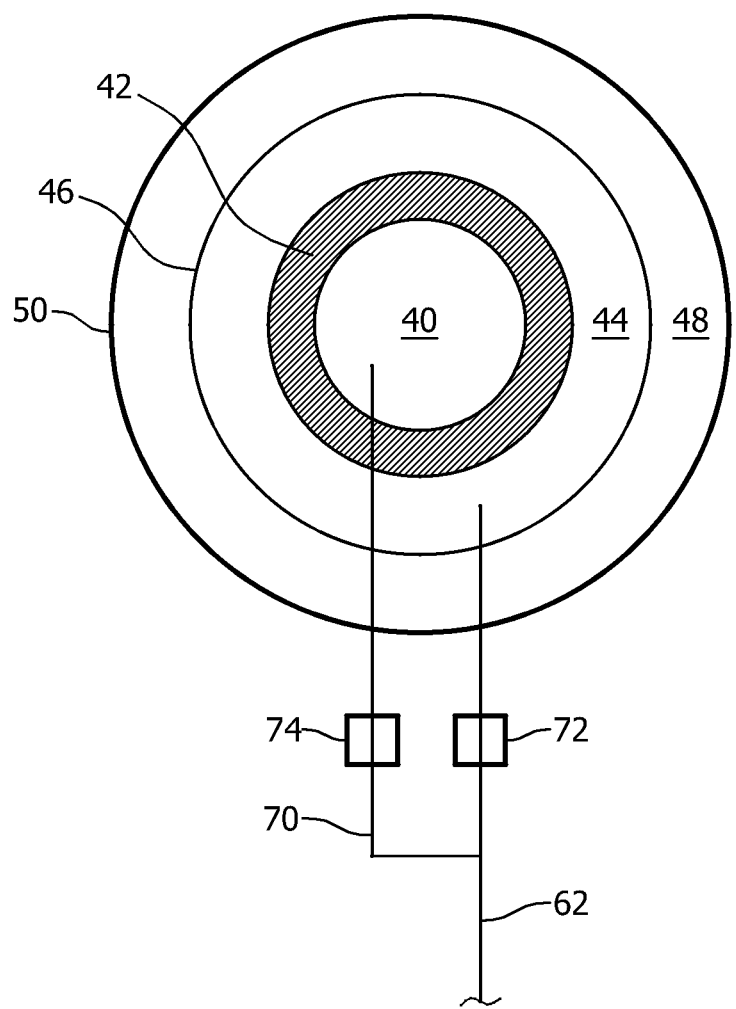
FIG. 2 shows a schematic cross sectional view of a membrane unit for using in an arrangement according to an embodiment of the invention.

FIG. 2 shows a cross sectional view of a preferred embodiment of the membrane unit 32. The membrane unit 32 may be of any configuration. However, a tubular shape of the membrane unit 32 is especially advantageous. At its inside, the membrane unit 32 may comprise an inner conduct, or a primary membrane chamber 40, respectively, being in flow connection with the conduit 20, and allowing the oxygen comprising gas to enter the membrane unit 32. The primary membrane chamber 40 is limited at its outside by a dense membrane 42, such as an inorganic membrane, the membrane 42 having a primary and a secondary side. The primary side is directed to the primary membrane chamber 40 and thus to the plasma pump 14, whereas the secondary side is directed to an outer conduct, or a secondary membrane chamber 44, respectively. The secondary membrane chamber 44 is limited at its inner side by the membrane 42 and at its outer side by an inner housing 46. Consequently, the membrane unit 32 preferably has a primary membrane chamber 40 being located at a primary side of the dense membrane 42 and a secondary membrane chamber 44 being located at a secondary side of the dense membrane 42, wherein the primary membrane chamber 40 and the secondary membrane chamber 44 are at least partly divided by the dense membrane 42. The inner housing 46 may be a tube made from a material being resistant against higher temperatures, for example quartz glass or ceramic aluminum oxide. The objective of the secondary membrane chamber 44 is to conduct the separated oxygen out of the membrane unit 32 and is thus in flow connection with the conduct 34. Outside the inner housing 46, a heat isolation 48 is provided. This may preferably be a vacuum, which is provided between the inner housing 46 and an outer housing 50. It is as well possible to provide an inert gas between the inner housing 46 and the outer housing 50. In this case, it would be preferable to provide a very short distance between the inner housing 46 and the outer housing 50 to achieve a sufficient isolation. However, the isolation 48 may be of any kind known from the state of the art to get a sufficient isolation effect. The outer housing 50 may be designed as a thermal shield, for example based on aluminum, to further improve the isolation. This in fact improves the energy efficiency of the arrangement 10 and is thus cost saving.

Referring back to the membrane 42, its objective is to separate the oxygen from the remaining retentate flow, i.e. the remaining constituents of the oxygen comprising gas, and thus to provide a flow of oxygen, which advantageously is a flow of 100% pure oxygen. Mostly, the main remaining constituent is nitrogen, especially in the case when air is used as oxygen comprising gas. To get sufficient separation results, it is thus essential that the membrane 42 is very dense. A dense membrane 42 is a membrane being permeable with respect to oxygen, but being strictly or at least substantially non-permeable for other gases, especially for nitrogen.

To achieve these properties, the membrane 42 may be a solid ceramic membrane comprising selected inorganic oxide compounds. Preferable inorganic membranes are mainly based on a Perovskite or Fluorite crystal structure. As an example, the Perovskite-related material $Ba_{0.5}Sr_{0.5}Co_{0.5}Fe_{0.2}O_{3-\delta}$ (BSCF) is very well suited. It is a general property of these kinds of inorganic membranes that they are completely impervious to all gases at room temperature, but allow oxygen molecules to pass through when heated to elevated temperatures. Mainly, temperatures above 700 K are necessary to achieve a good oxygen flow with the requirement of only small sized membranes. For example, the above named BSCF may come up with an oxygen flow of 13 ml/cm$^2$min at 1275K, wherein a membrane thickness of only 0.2 mm is sufficient.

The membrane 42 may be either a pure oxygen conducting membrane or mixed ionic-electronic conducting membrane. Generally, a force has to be applied to cause the oxygen being transferred through the membrane 42. This may either be an electronic force. However, it is preferred, that the oxygen passes the membrane 42 due to a pressure difference between the primary and the secondary side of the membrane 42.

The compression of the oxygen comprising gas in the plasma pump 14 at the same time leads to a pressure difference between the primary side and the secondary side of the membrane 42. Due to this effect, an increased oxygen partial-pressure at the primary side is generated enabling an oxygen flow through or a transfer across the dense membrane 42, respectively. This flow may further be enhanced by providing a reduced pressure on the secondary side of the membrane 42 instead of an increased pressure at the primary side of the membrane 42 or additionally thereto. Under extreme conditions, a vacuum may be provided on the secondary side of the membrane 42 to provide a sufficiently high oxygen flow through the membrane 42.

Without using a reduced pressure on the secondary side, it is preferable to use pressures of ≥2.5 bars upstream the membrane 42, thus on its primary side. Here, it is especially preferable to use pressures lying in the range of 5 bars or ≤5 bars. Depending from the temperature of the membrane 42 and the dimensions of the latter, an oxygen flow with a modest elevation compared to atmospheric pressure, approximately 1 bar may be achieved at the outlet 38. This may achieved with a pressure of the oxygen comprising gas being sensibly reduced with respect to the state of the art. The pressure range according to the invention is especially suitable for home care applications.

It is apparent, that the membrane 42 has to be stable enough to stand these conditions like described above. This is especially important, as it is preferred to form the membrane 42 in a very small size or thickness. Especially, by providing an extensive pressure gradient between the primary side and the secondary side of the membrane 42, it may be advantageous to fix the membrane 42 on a support. The support may be formed as a porous membrane, in particular a thick inorganic membrane like used for coarse filters. A porous membrane as referred to in this case is a membrane being permeable for gases and non-selective with respect to oxygen. This enables an enhanced stability of the membrane 42 without the requirement of forming the membrane 42 as such more stable. This further reduces costs, as the stable and forming component is the membrane support, which is much cheaper than the membrane 42 as such.

Like stated above, it may be essential to heat the membrane 42 to get sufficient oxygen permeability. According to the invention, this may be achieved in an easy and simple way. By providing a plasma pump 14 for compressing the oxygen comprising gas, the compressed gas at the same time is heated to a temperature range being sufficiently high to heat the membrane 42 to its operational temperature. Exemplary temperature ranges are temperatures ≥700K. It is especially preferable to heat the oxygen comprising gas and thus the membrane 42 to ranges of ≥1000K to ≤1300K. In these temperature ranges, very suitable oxygen flows may be achieved and furthermore, the generation of nitric oxide will be improved, like will be apparent down below.

Referring back to FIG. 1, the membrane unit 32 furthermore comprises an outlet 52 which is connected on the one side to the primary membrane chamber 40 and on the other side may be connected to the atmosphere. Through the outlet 52, gas with reduced oxygen content, especially nitrogen, leaves the membrane unit 32. This is the exhaust gas of the membrane unit 32. The outlet 52 may comprise a further valve 54, which is especially advantageous, if a pressure is provided inside the primary membrane chamber 40.

Downstream the membrane unit 32, like stated above, the conduct 34, which may comprise a further valve like a non return valve, is connected to the outlet 38. The outlet 38 may be equipped with a mouthpiece 56 or the like, enabling a direct administration of the generated oxygen. Thus, an additional valve or a small compressor may be provided for a sufficient flow of pure oxygen.

According to the invention, additionally to the generation of oxygen, nitric oxide is generated. This step is performed by providing a stream of nitrous oxide comprising gas being heated to a temperature, at which nitric oxide is generated. Therefore, the arrangement 10 comprises a device being designed for heating a flow of nitrous oxide comprising gas being egressed from the source of nitrous oxide comprising gas to a temperature, at which nitric oxide is generated, using heat generated in the process of operating the membrane (42). This may for example be a heat exchanger. However, it is preferred that the arrangement 10 further comprises a conduit 62 being arranged to guide a nitrous oxide comprising gas to the primary side of the membrane 42, for example into a primary membrane chamber 40 and/or a conduit 70 being arranged to guide a nitrous oxide comprising gas to the secondary side of the membrane 40, for example into the secondary membrane chamber 44 in the membrane unit 32. The conduit 62 and/or the conduit 70 may be connected to a source 58 of nitrous oxide comprising gas. The source 58 may either comprise pure nitrous oxide or a mixture of nitrous oxide in a carrier gas, preferably in a concentration allowing providing the nitrous oxide comprising gas in the primary membrane chamber 40 in the range of ≤2 vol-% and in the secondary membrane chamber 44 in the range of ≤0.1 vol-%. In case nitrous oxide is provided in a carrier gas, it is preferred to use nitrogen as carrier gas.

Preferably, pure nitrous oxide may be used as nitrous oxide comprising gas and may be guided into the respective membrane chamber 40, 44. Alternatively, the nitrous oxide comprising gas is formed by mixing nitrous oxide with a small amount of a gas flow being generated at the primary side of the membrane 42, i.e. in the primary membrane chamber 40. With this regard, a conduit 60 may be connected to the outlet 52 in order to guide a stream of gas being depleted with respect to oxygen to the conduit 62 and/or to the conduit 70 guiding the nitrous oxide comprising gas into the membrane unit 32. Therefore, the valve 54 may be provided in the outlet 52 downstream the conduit 60 in order to reduce or to permit the flow of the gas into the atmosphere, or out of the arrangement 10, respectively, but to enhance the flow into the conduit 60. In detail, the conduit 60 may be connected to a gas mixing device 66 in order to mix pure nitrous oxide or a nitrous oxide comprising gas with the gas stream coming from the primary side of the membrane 42. In order to achieve the desired concentration, a valve 68 which may regulate the gas flow may be provided in the conduit 60. Together with the provision of a flow regulator of the gas source 58, the required concentration of nitrous oxide comprising gas may be achieved.

Again with respect to the conduits 62, 70 guiding the nitrous oxide comprising gas into the membrane unit 32, only the conduit 62 may be provided guiding the nitrous oxide comprising gas into the membrane unit 32 and in detail into the primary membrane chamber 40. Alternatively, only the conduit 70 may be provided guiding the nitrous oxide comprising gas into the membrane unit 32 and in detail into the secondary membrane chamber 44. In an especially preferred embodiment of the present invention, both conduits 62 and 70 are provided together and joined to each other. This enables to guide the nitrous oxide comprising gas both to the primary and the secondary side of the membrane 42, for example into the primary membrane chamber 40 and the secondary membrane chamber 44 of the membrane unit 32, or solely to the primary side of the membrane 42 or the secondary side of the membrane 42 of the membrane unit 32. In order to select the side at which the nitrous oxide comprising gas is guided to, a valve 72 may be provided in the conduit 62, whereas a valve 74 may be provided in the conduit 70. By use of the valves 72, 74, the stream of nitric oxide comprising gas may be regulated in the desired way.

By guiding the nitrous oxide comprising gas close to the hot membrane 42 in the respective membrane chamber 40, 44, nitrous oxide will react to form nitric oxide due to the fact that the membrane 42 and thus the nitrous oxide comprising gas exhibits a temperature at which nitrous oxide may react to form nitric oxide.

In case the reaction takes place in the primary membrane chamber 40, nitric oxide will be generated in an atmosphere comprising mostly nitrogen. The generated nitric oxide comprising gas may then be guided out of the outlet 52. It may then be stored or used directly, for example by guiding it into an administration device for a patient. In the latter case, the nitric oxide comprising gas may be cooled before administering it to a patient. With this regard, it is especially preferred that the nitric oxide comprising gas is cooled to room temperature in a time range of ≤10 s, in particular ≤1 s. This ensures that no undesired side products are formed downstream the reaction chamber. Furthermore, these cooling speeds are in any case short enough to apply the method according to the invention to in situ applications. Alternatively, the nitric oxide comprising gas may be guided through a conduit 76, for example by closing a valve 78, to the outlet 38 and thus into the stream of pure oxygen. It may thus be administered in one step with the oxygen. It may further be administered in a pulsed way, i.e. in pulses of nitric oxide comprising gas being arranged between pulses of oxygen. Therefore valves 80 and 82 may be provided in the conduit 70 and in the outlet 38 in order to generate the respective gas streams. It is apparent that in this case the nitrous oxide comprising gas is not intermixed with the retentate flow being generated at the primary side of the membrane 42, as this flow includes nitric oxide.

In case the reaction takes place in the secondary membrane chamber 44, nitric oxide will be generated in an atmosphere comprising mostly oxygen. Due to the fact that the temperature of both gases lies in a range in which the generation of nitrogen dioxide is inhibited like described above, the resulting gas mixture of nitric oxide and oxygen may be administered to a patient directly through the outlet 38 by cooling it shortly before the administration step.

According to a further embodiment, the flow of nitrous oxide comprising gas may be guided into a stream of gas being depleted with respect to oxygen downstream the primary membrane chamber 40. Therefore, a conduit 84 may be provided being connected to the source 58 of nitrous oxide and to the conduit 76. By controlling the valve 78 and a valve 86 in the conduit 76 between the outlet 52 and the conduit 84, a small amount of the retentate flow being generated in the primary membrane chamber 40 may be branched of and may be mixed with the nitrous oxide comprising gas. Due to the fact that the retentate flow of gas being depleted with respect to oxygen still exhibits elevated temperatures, the nitrous oxide may react to form nitric oxide. The so formed nitric oxide comprising gas may then be guided through an outlet 88 and may be used directly or it may be stored. The storage should not lead to serious problems due to the fact that the main constituent thereof is nitrogen. Alternatively, a valve 90 being located in the outlet 88 may be closed because of which the nitric oxide comprising gas may be guided through the conduit 76 and may be mixed in the outlet 38 with the generated oxygen.

However, the nitrous oxide comprising gas may additionally be guided into the stream of oxygen comprising gas being branched off upstream the membrane unit 32, especially with heated oxygen comprising gas. This allows forming a nitric oxide comprising gas independent from the stream of oxygen depleted gas or oxygen. This embodiment is especially suited for non-therapeutic applications, as the formation of nitrogen dioxide may be stronger with respect to guiding the nitrous oxide comprising gas in the oxygen depleted gas or oxygen.

In any case, the reaction time of the nitrous oxide comprising gas preferably lies in a range of ≥10 ms to ≤100 s. This reaction time may be adjusted by adjusting the flow rate of the nitrous oxide comprising gas. Referring to this, SATP flow rates of the nitrous oxide comprising gas of ≥0.01 $L_{SATP}$/min to ≤10 $L_{SATP}$/min are preferred.

Additionally, it may be preferred that the water content of the gas being present in the membrane unit 32 lies in a range of ≤1 vol-%. This enables the method according to the invention to be carried out substantially in the absence of water. A substantially water-free atmosphere may be important as water often inhibits the decomposition of nitrous oxide to nitric oxide and leads to the formation of nitrogen dioxide in high concentrations. The desired water content may be adjusted by using respectively dry gas sources. To ensure that the water content is not increased and furthermore to reduce the water content by using gas sources with a slightly higher water content, water adsorbing substances may be provided, in particular in the conduits 20, 62, 70, 84. As an example dried silica gel or dried zeolites or hygroscopic substances as e.g. phosphorus pentoxide may be used as a coating or as a plug inside the respective conduits upstream the membrane unit 32.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. Method of generating a gas comprising both oxygen and nitric oxide, said method comprising the steps of:
    guiding an oxygen comprising gas to a primary side of a dense membrane, wherein the dense membrane is permeable for oxygen but non-permeable for other gases,
    heating the membrane to a temperature at which it is permeable for oxygen,
    creating a pressure difference between the primary side of the membrane and a secondary side of the membrane, wherein a stream of oxygen is generated at the secondary side of the membrane and a stream of oxygen depleted gas is generated at the primary side of the membrane, wherein said method further comprises the steps of
    providing a flow of nitrous oxide comprising gas,
    heating the nitrous oxide comprising gas to a temperature at which nitric oxide is generated, thereby using heat generated in the process of operating the membrane.

2. Method according to claim 1, wherein the flow of nitrous oxide comprising gas is guided into one of the stream of oxygen and the stream of oxygen depleted gas.

3. Method according to claim 1, wherein the oxygen comprising gas is compressed in order to create a pressure difference between the primary side and the secondary side of the membrane.

4. Method according to claim 3, wherein the oxygen comprising gas is compressed by a plasma pump.

5. Method according to claim 3, wherein the oxygen comprising gas is compressed to a range of ≥2.5 bars.

6. Method according to claim 1, wherein the nitric oxide comprising gas is formed by mixing nitrous oxide with at least a part of the oxygen depleted gas.

7. Method according to claim 1, wherein nitric oxide is generated based on a gas in which nitrous oxide is present in a concentration in the range of ≤2 vol-%.

8. Method according to claim 1, wherein air is used as oxygen comprising gas.

9. Method according to claim 1, wherein the oxygen comprising gas is heated to a temperature in the range of ≥1000K and ≤1300K.

10. Method according to claim 1, wherein the generated oxygen is cooled after separation.

11. Method according to claim 1, wherein the reaction time of the nitrous oxide comprising gas lies in a range of ≥10 ms to ≤100 s.

12. Method according to claim 1, wherein SATP flow rates of the nitrous oxide comprising gas of ≥0,01 $L_{SATP}$/min to ≤10 $L_{SATP}$/min are used.

13. Arrangement for generating a gas comprising both oxygen and nitric oxide, the arrangement comprising
   a source of oxygen comprising gas,
   a dense membrane having a primary side and a secondary side, wherein the dense membrane is permeable for oxygen but non-permeable for other gases,
   a device for creating a pressure difference between the primary side and the secondary side of the membrane, and
   a device for heating the membrane, wherein the arrangement further comprises
   a source of nitrous oxide comprising gas, and
   a device being designed for heating a flow of nitrous oxide comprising gas being egressed from the source of nitrous oxide comprising gas to a temperature, at which nitric oxide is generated, using heat generated in the process of operating the membrane.

14. Arrangement according to claim 13, wherein the device being designed for heating a flow of nitrous oxide comprising gas comprises a conduit being arranged to guide the nitrous oxide comprising gas to the primary side of the membrane or to the secondary side of the membrane.

15. Arrangement according to claim 13, wherein the device being designed for heating a flow of nitrous oxide comprising gas comprises a heat exchanger.

* * * * *